United States Patent [19]

Chang et al.

[11] Patent Number: 4,661,623

[45] Date of Patent: Apr. 28, 1987

[54] METHOD OF PRODUCING METHYL FORMATE FROM METHANOL AND CARBON MONOXIDE USING ANIONIC GROUP VIII METAL CATAYSTS

[75] Inventors: Biau-Hung Chang, Worthington; Robert A. Grimm, Upper Arlington, both of Ohio; Bhupendra C. Trivedi, Nizampura, India

[73] Assignee: Ashland Oil, Inc., Columbus, Ohio

[21] Appl. No.: 713,449

[22] Filed: Mar. 19, 1985

Related U.S. Application Data

[63] Continuation-in-part of Ser. No. 467,023, Feb. 16, 1983, abandoned.

[51] Int. Cl.$^4$ ............................................. C07C 67/36
[52] U.S. Cl. ..................................................... 560/232
[58] Field of Search ......................................... 560/232

[56] References Cited

U.S. PATENT DOCUMENTS

| | | | |
|---|---|---|---|
| 3,816,513 | 6/1974 | Wakamotsu et al. | 560/232 |
| 4,420,633 | 12/1983 | Furusaki et al. | 560/232 |

FOREIGN PATENT DOCUMENTS 3221239  12/1982  Fed. Rep. of Germany ...... 560/232

Primary Examiner—Werren B. Lone
Attorney, Agent, or Firm—Wood, Herron & Evans

[57] ABSTRACT

A method of producing methyl formate from methanol and carbon monoxide using an anionic transition metal catalyst including a metal selected from Fe, Ru, Os, W, Mo, Cr, Co, Rh and Ir. The reaction is characterized as a low pressure reaction conducted at a pressure less than 3,000 psia and using concentrated anhydrous methanol solutions and, preferably neat methanol. The catalyst can be a mixed metal catalyst including a second metal selected from Group VIII metals. The reaction is highly selective towards methyl formate and excellent turnover numbers are obtained using these catalysts.

12 Claims, No Drawings

METHOD OF PRODUCING METHYL FORMATE FROM METHANOL AND CARBON MONOXIDE USING ANIONIC GROUP VIII METAL CATAYSTS

RELATED APPLICATION

This application is a continuation-in-part of Ser. No. 467,023, filed Feb. 16, 1983, now abandoned.

The present invention relates to a method of making methyl formate at low reaction pressures using methanol and carbon monoxide in the presence of a catalyst.

The present invention further relates to a method of producing methyl formate from carbon monoxide and methanol using an anionic Group VIII transition metal catalyst wherein the metal is Fe, Ru, Os, W, Mo, Cr, Co, Rh or Ir.

Methyl formate is a useful precursor in the production of formic acid currently used to assist in the preservation and drying of crops, particularly in more northern areas of the world where drying seasons are short. Methyl formate is typically produced in a low pressure reaction, i.e., under 3,000 psia from methanol and carbon monoxide in the presence of a catalyst. The catalyst typically is an alkaline or alkali metal methoxide, such as sodium methoxide. This reaction, from a positive point of view, is conducted under non-severe pressure conditions (i.e., well under 3,000 psia); however, the turnover numbers obtained using these catalysts is relatively low. Turnover number is the number of moles of product produced divided by the number of moles of catalyst used per hour. Typically, using the alkaline metal methoxide, turnover numbers below about 20 are observed. Furthermore, these catalysts are corrosive. This in turn reduces the useful life of a reactor, increases reactor cost and increases maintenance costs. Therefore, a more efficient, less caustic catalyst is preferred.

Choosing a different catalyst presents the problem of finding a catalyst which is as efficient or more efficient than prior art catalysts. Furthermore, if the new catalyst is to be used in existing plants, the catalyst must function at lower pressures.

Transition metal catalysts, including Group VIII metal catalysts, are used in the reaction of hydrogen and synthesis gas (syngas) to produce alcohols. There is extensive literature in this area reporting the use of a wide variety of catalysts under a wide variety of reaction conditions. These reactions do produce methyl formate as a by-product in minor or trace amounts. Of course, with these prior art methods, the goal is not the production of methyl formate. Therefore, the prior art fails to appreciate the significance of reacting substantially pure methanol or methanol even in concentrations greater than 15 molar percent with carbon monoxide to produce methyl formate. These references can all be characterized in that methyl formate is a by-product and is produced in only slight amounts with low selectivity.

SUMMARY OF THE INVENTION

The present invention is premised upon the realization that certain anionic Group VIII transition metal catalysts can be used to catalyze the production of methyl formate from methanol and carbon monoxide at low pressures. The methanol in this reaction should be at least 15 molar percent methanol, and preferably, neat methanol to react with the carbon monoxide. This reaction can be conducted at low pressures, generally less than about 3,000 psia and preferably from 1500 psia to about 2,300 psia. The turnover numbers produced when using these catalysts are excellent and the selectivity towards methyl formate is in excess of 99%. The general formula for catalysts for use in the present invention is:

$$M^{+n}[H_yA_x(L)_z]^{-n} \quad (I)$$

wherein A is selected from Fe, Ru, Os, W, Mo, Cr, Co, Rh and Ir. M is a cation, L is a ligand and n represents the numerical value of the charge.

DETAILED DESCRIPTION

The catalytic carbonylation of methanol is accomplished in a reactor designed for efficient gas liquid contact and mass transfer capable of withstanding pressures up to about 3,000 psia and temperatures up to about 200° C.

Generally, liquid methanol with catalysts dispersed therethrough is admitted into the reactor. The reactor is then pressurized to the desired pressure with carbon monoxide, and the reaction will commence on its own aided by agitation. The reactor can be heated to the desired temperature or can be heated only by the heat of reaction.

The methanol can be neat or a solution of methanol dissolved in a solvent such as tetrahydrofuran. However, the methanol and solvent must be anhydrous. Preferably, the methanol concentration will be greater than 15 molar percent. Since methanol concentration is very important, the concentration should be higher, such as 50% or more, preferably 90%. Most preferably, the methanol is neat methanol. When the methanol concentration is below 15 molar percent, turnover rate is substantially decreased. Typically, in this reaction, substantially pure methanol is used without any solvent.

The carbon monoxide can be in the form of a relatively high purity carbon monoxide, such as a by-product of electrometallurgical furnace or synthesis gas. The carbon monoxide must also be anhydrous. It is compressed for feeding into the reactor. The highest conversions are obtained using a high feed gas purity. The purities as low as 50% may work, but would require a higher gas throughput and higher compression costs. Sufficient carbon monoxide is provided to react with the methanol by maintaining the pressure within a reactor at about a constant. Stoichiometrically, a substantial excess of carbon monoxide is present.

The catalysts of the present invention is either an anionic transition metal compound having the general formula:

$$M^{+n}[H_y A_x (L)_z]^{-n} \quad (II)$$

or a mixed transition metal compound: having the following general formula

$$M^{+n}[H_y A'_Q A_x (L)_z]^{-n} \quad (III)$$

In formulas II and III
A represents Fe, Ru, Os, W, Mo, Cr, Co, Rh or Ir;
A' represents a Group VIII transition metal;
M is a cationic species;
L is a ligand;
n is an integer greater than or equal to 1 and preferably greater than 1;
x is an integer greater than or equal to 1;
y is an integer greater than or equal to 0;

Q is an integer greater than or equal to 0; and z is an integer less than or equal to the available coordination bonding sites of the transition metal complex represented by $A_x$ or $A'_Q A_x$.

Typically, n will not exceed 6, y will not exceed 4 and is usually 2 or less, x and Q combined will not exceed about 36. In theory, these upper limits may be exceeded, but known species generally fall within these limits. When Q is 0, formulas II and formula III are the same.

The ligands represented by L include any ligand which will bond with the transition metal complexes and which will not interfere with the carbonylation reaction. Ligands specifically suitable for use in the present invention include: trialkyl phosphines, trialkyl arsines, trialkyl antimonies, trialkyl bismuths, triaryl phosphines, triaryl arsines, triaryl antimonies, triaryl bismuths, tertiary amines, carbon monoxide and halides. As shown in the examples, carbon monoxide is typically preferred.

In the present invention, one of ordinary skill in the art can easily choose an appropriate ligand. The following should be considered as an exemplary list of appropriate ligands and is supplied by way of example and is not intended to be limiting.

These include, for example, carbon monoxide, isocyanides, substituted phosphines, arsines, stibenes, sulfides, nitric oxides, and various molecules with delocalized Pi orbitals such as pyridine, bipyridine, phenanthroline, dithioketone, dithioline, as well as others. Further, dinitrogen compounds can be used along with carbonmonosulfide and thiocarbonyl complexes. Trivalent phosphorous compounds such as trihalophosphorous, triphenylphosphorous, trioxymethylphosphine, as well as corresponding arsenic and antimony compounds can be used. Nitrogenous compounds such as nitric oxide, isocyanides such as phenylisocyanide and methlyisocyanides also form suitable ligands. Complexes of unsaturated organic molecules such as alkenes, ethene, butene, propene and the like as well as conjugated alkenes such as 1-3,butadiene, alkynes and aromatic molecules can form ligands. Such aromatic ligands would include $C_4H_4$, $C_5H_5$, $C_6H_6$, $C_8H_8$, and $C_7H_7$. Hydrido anions such as tetrahydroboron, tetrahydrofuran are suitable ligands. Organometallic compounds can also form suitable ligands. These would include, for example, trialkyl and triaryl compounds of boron, gallium, indium, thallium, and aluminum. Cyanide also readily acts as a ligand in the present invention. Carbon disulfide and carbon dioxide also have utility as ligands. Suitable ligands formed from silicon, germanium and tin include trialkyl and triaryl silicon germanium or tin compounds. Trihalo anions such as trichlorotin are also suitable compounds. Ligands which are formed from or derivatives of ammonium or amines include, triethylenediamine, diimine complexes such as ortho-benzoquinonediimine, polyamines such as bipyridine, phenanthroline and terpyridine, as well as pyridazine, pyrimidine, purine, pyrazine, naphthyridine, pyrazolate, imidazolate. Other imidazoles can also form suitable ligands. Ligands can also be derived from deprotonization of ammonia and amines such as dialkylamido nitrene and nitrido complexes. Suitable ligands with conjugated Pi systems would include phthalocyanines, porphyrins, benzthiaazoline.

Shiff base ligands suitable for use in the present invention include, polypyrazolylborate ligand, nitriles, oximes and C-nitroso compounds. Monoximes for example would include 2(2-hydroxyethyl) imino-3-oximobutane.

Trialkyl and triaryl phosphorous, arsenic antimony, bismuth compounds as well as multidetentate ligands such as diphosphine ligands and hetrocyclic compounds such as phosphole are suitable ligands. Hydroxide and oxide ions also form suitable ligands. Various organic compounds such as ethers, ketones and esters can form ligand bonds to transistion metals according to the present invention, as well as thio ethers, dithiolenes and halide ions.

Since the catalysts of the present invention are anionic, the ligands preferably should not act as oxidizing or protonating agents. Therefore, less preferred ligands include water, nitrate compounds, nitrite compounds, perchlorates, phosphorous oxoacids, sulfur oxoacids and hydrogen sulfides. These tend to oxidize or protonate the catalyst and accordingly decrease its efficiency.

Particularly suitable ligands for use in the present invention include trialkylphophines such as trimethylphosphine, triethylphosphine, tributylphosphine, tripropylphosphine, tripentylphosphine, trihexylphosphine, triheptylphosphine, trioctylphosphine and so on, up to $C_{22}$. Particularly suitable triallylphosphines include tribenzylphosphine, tris-(2-cyanoethyl)phosphine, tris(3-diethylaminopropyl) phosphine, tricyclohexylphosphine, bis(1,2-dibutylphospheno) ethane, bis(1,2-dicyclohexylphospheno) ethane, bis(1,2-diethylphospheno) ethane, bis(1,2-dimethylphospheno) ethane, bis(dimethylphospheno) methane, bis(1,2-dipropylphospheno) ethane.

Suitable triaryl phosphines and mixed tertiary phosphines include triphenylphosphine, tri(chlorophenyl) phosphine, trinaphthyl phosphine, tri(fluorophenyl) phosphine, tris(methoxyphenyl) phosphine, tritolylphosphine, tris(2-diphenylphosphinoethyl) phosphine, allyldiphenyl phosphine, benzyldiphenyl phosphine, bis(3-aminopropylphenyl) phosphine, bis(2-cyanoethylphenyl) phosphine, bis(1,2-diphenylphosphino)-benzene, bis(1,4-diphenylphosphino) benzene, bis(1,4-diphenylphosphino) butane, bis(1,2-diphenylphosphino) ethane, bis(1,2-diphenylphosphino) ethylene, bis(2-diphenylphosphinoethyl) phenyl phosphine, bis(1,6-diphenylphosphino) hexane, bis(diphenylphosphino) methane, bis(1,5-diphenylphosphino) pentane, bis(1,2-diphenylphosphino) propane, bis(1,3-diphenylphosphino) propane, bis ($\alpha,\alpha$-diphenylphosphino)-0-xylene, bis(1,2-ditolylphosphino) ethane, bromobenyldiphenylphosphine, butyldiphenylphosphine, 2-cyanoethyldiphenylphosphine, cyclohexyldiphenylphosphine, diallylphenylphosphine, diarylphenylphosphine, dibutylphenylphosphine, dicyclohexylphenylphosphine, diethylphenylphosphine, 1-diethylphosphino-2-diphenylphosphino ethane, diheptylphenyl phosphine, dihexylphenyl phosphine, dimethylphenyl phosphine, dimethyltolyl phosphine, diphenylenephenyl phosphine, ditolylphenyl phosphine, divinylphenyl phosphine, ethyldiphenyl phosphine, hexyldiphenyl phosphine, 1,1,4,7,10,10-hexylphenyl-1,4,7,10,-tetraphosphadecane, methoxyphenyldiphenylphosphine, (2-methylbutyl)diphenyl phosphine, methyldiphenyl phosphine, methylethylphenyl phosphine, pentafluorphenyldiphenyl phosphine, propyldiphenyl phosphine.

Ligands analagous to the above phosphine ligands can be made wherein the phosphorous is replaced with arsenic, animony, bismuth or nitrogen. Other preferred ligands are the halides, hydride and most suitable is carbon monoxide. A thorough description of ligands is contained in *Advanced Inorganic Chemistry, A Comprehensive Text*, by Cotton & Wilkinson, 4th Edition, published by John Wiley & Sons, Copyright 1980, pages 75-193.

M can represent any cationic species which will bond to the transition metal anionic complex and will not interfere with the carbonylation reaction. Generally, M will represent one or more metal atoms selected from metals in Group IA and Group IIA of the Periodic chart or an organic cation such as iminium, ammonium, phosphonium or arsenium.

The cations or counterions useful in the present invention include ionic lithium, sodium, postassium, rubidium, cesium, fransium, berylium, magnesium, calcium, strontium, barium, radium, aluminum, indium, telurium, as well as ammonium, $[N(R_1)(R_2)(R_3)(R_4)]^+$ wherein $R_1$, $R_2$, $R_3$ and $R_4$ represent hydrogen, alkyl, substituted alkyl, aryl or substituted aryl, for example, tetramethyl ammonium or dimethyl diethyl ammonium. Further, phosphonium and arsenium cations are also suitable. Imminium compounds can also be suitable cations for the present invention, such as $[(R_1)(R_2)(R_3)P]_2N^+$ wherein $R_1$, $R_2$ and $R_3$ represent alkyl, substituted alkyl, aryl or substituted aryl, for example $[(C_6H_5)_3P]_2N^+$. Of course more complex ions such as $[Ni(NH_3)_6]2^+$, $[Co(C_5H_5)_2]^+$, $[Ni(phen)_3]^{+2}$, $[Fe(C_5H_5N)_6]^{+2}$, $[Fe(phen)_3]^{+2}$, $[Fe(NH_3)_6]2^+$, $[Cr(C_6H_5—C_6H_5)_2]+1$, wherein phen represents phenanthroline are also suitable cations. In the present invention, the catalyst works in solution. Accordingly, these cations only act as counterions. The selection of appropriate cation does not form an inventive feature of the present invention.

Accordingly, the present invention is not limited by the selection of an appropriate cation or ligand. One of ordinary skill in the art can easily choose appropriate counterions and ligands in the present invention.

In the production of methyl formate the catalyst goes into solution and accordingly has either the following general formulas during the reaction:

$[H_yA_x(L)_z]^{-n}$ 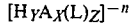 IV $[H_yA'_{Q}A_y(L)_z]^{-n}$ 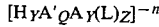 V

The anionic transition metal catalyst represented by formula II can be prepared by the reduction of a neutral species such as metal carbonyls or the deprotonization of hydride metal compounds.

For example, $[(Ph_3P)_2N]_2[Fe_3(CO)_{11}]$ can be prepared from $Fe_3(CO)_{12}$. More specifically, the $Fe_3(CO)_{12}$ can be reacted with KOH dissolved in absolute methanol at room temperature for about 28 hours. The addition of $(Ph_3P)_2NCl$ causes $[(Ph_3P)_2N]_2[Fe_3(CO)_{11}]$ to precipitate out of solution. This is further described in Hieber, W.; Brendel, G.Z., *Anorg. Allg. Cheml.*, 1957, 289, 324-337.

As discussed in Collman et al., *Oxidative-Addition Reactions of the $Na_2Fe(CO)_4$ Supernucleophilies*, J. American Chem. Soc., 94, 2515 (1977), $Na_2Fe(CO)_4$ and analogous compounds can be prepared by the reduction of $Fe(CO)_5$ using sodium dispersed in benzophenone. $K_2Fe(CO)_4$ can be prepared in a similar manner.

The preparation of $[Os_3(CO)_{11}]^{2-}$ is discussed in Nagel et al., *Synthesis of New Trinuclear Ions $[Ru_3(CO)_{11}]^{2-}$, and $]Os_3(CO)_{11}]^{2-}$ in J. of Organometallic Chemistry*, 219 (1981) C9-C12. These compounds are prepared by the reduction of the neutral species using, for example, an alkali metal benzophenone solution.

The anionic ruthenium compounds may be produced according to numerous methods disclosed in the following articles: Eady et al., *Improved Synthesis of the Hexanuclear Clusters $[Ru_6(CO)_{18}]^{2-}$, $[HRu_6(CO)_{18}]^-$, and $H_2Ru_6(CO)_{18}$*, 1980 J.C.S. Dalton, 383; Inkrott et al., *Stepwise Deprotonation of $H_4Ru_4(CO)_{12}$: High-Yield Synthesis and Carbon-13 NMR Spectra of $H_3Ru_4(CO)_{12}^-$ and $H_2Ru_4(CO)_{12}^{2-}$*, 18 Inorganic Chemistry 2817 (1979); Inkrott et al., *The New Cluster Dianion $H_2Ru_4(CO)_{12}^{2-}$*, 100:12 Journal of the American Chemical Society 3954 (1978); P. F Jackson et al., *$H_2Ru_6(CO)_{18}$, $[HRu_6(CO)_{18}]^-$*, J.C.S. Chem. Com., 735 (1979); Nagel et al., *High Yield Synthesis of New Tetraruthenium Carbonylates: $[Ru_4(CO_{13}]^{2-}$, $[HRu_4(CO)_{13}]^-$, and $Ru_4(CO)_{12}]^{4-}$*, J.C.S. Chem. Com., 530 (1980); which are incorporated herein by reference to indicate the state of the art in anionic Group VIII complex chemistry.

Anionic ruthenium compounds are formed, for example, by the stepwise deprotonation of $H_4 Ru_4 (L)_z$ according to the following formula:

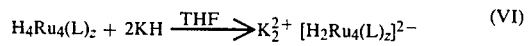

$$H_4Ru_4(L)_z + 2KH \xrightarrow{THF} K_2^{2+} [H_2Ru_4(L)_z]^{2-}$$ (VI)

wherein L represents a ligand and z is an integer corresponding to the number of available coordination bonding sites. When $H_2Ru_4(CO)_{12}^{2-}$ is being formed, the reaction is conducted by mixing the KH with the $H_4Ru_4(CO)_{12}$ in THF for about one half an hour at 55° C. and an additional 24 hours at ambient temperatures, both in an inert atmosphere. Removal of the solvent in vacuo yields $K_2[H_2Ru_4(CO)_{12}]$. The reaction product can be further reacted with two equivalents of $[(Ph_3P)_2N]Cl$ or $[(n—C_4H_9)_4N]Br$ to produce $[(Ph_3P)_2N]_2H_2Ru_4(CO)_{12}]$ and $[(n—C_4H_9)_4N]_2 [H_2Ru_4 (CO)_{12}]$, respectively.

Another method of producing the ruthenium anionic catalysts for use in the present invention is the controlled reduction of $Ru_3(L)_z$ using potassium-benzophenone according to the following reaction:

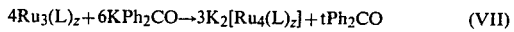

$$4Ru_3(L)_z + 6KPh_2CO \rightarrow 3K_2[Ru_4(L)_z] + tPh_2CO$$ (VII)

The reaction should be conducted in a dry, inert atmosphere, such as argon or nitrogen. A more specific example is the reduction of dodecarbonyltriruthenium by treatment with 1.6 equivalents of potassium-benzophenone (1% excess) in THF. A deep red solution is produced after stirring the solution overnight at $-78°$ C. and for 24 hours at 25° C. $K_2[Ru_4(CO)_{13}]$ is then obtained from this solution by precipitation with $CH_2Cl_2$. The deep red reaction mixture can be further reacted with $[(Ph_3P)_2N]Cl$ and precipitated with $CH_2Cl_2$ to yield $[(Ph_3P)_2N]_2 [Ru_4(CO)_{13}]$.

Dianionic osmium, tungsten, molybdenum, chromium, cobalt, rhodium and iridium compounds can also be formed using similar methods. Specifically, neutral compounds can be reduced using appropriate reducing agents such as sodium amalgam in tetrahydrofuran.

Mixed metal catalysts depicted in formula III are complexes of transition metal compounds which contain two transition metal compounds. The compounds are known, and there are various methods to produce these compounds, such as reaction of carbonylmetalates with metal halides. This and other methods of production are discussed in 18 *Advances in Organometallic*

Chemistry, 207 which is incorporated herein by reference to indicate the state of the art in mixed metal chemistry.

The concentration of catalyst with respect to methanol is generally quite low. A range of concentrations is shown in the examples, and may range from 0.3 molar percent to about 0.05 molar percent.

To produce methyl formate according to the method of the present invention, the catalyst, together with the alcohol, is admitted into a reactor. The reactor is a vessel which can be pressurized and provides adequate mixing. The reactor can be a batch or continuous-type reactor provided the continuous reactor provides sufficient time for the alcohol to react with the carbon monoxide and the carbon monoxide can be maintained in solution. The reactor is pressurized to the desired pressure with carbon monoxide. The reagents are then maintained in an agitated condition during the reaction.

The upper pressure limit is partially a function of reactor capability. However, the present invention is operable at less than 3,000 psia. The preferred pressure is actually determined by balancing considerations of productivity, reactor costs and reactor capability. As shown in the examples, good results are obtained at 1000 psia and up to 2400 psia. Higher pressures do not seem to significantly improve yield. Although these catalysts will function at higher than 3,000 psia, reactor costs would be prohibitive. Based on the examples and considering reactor costs, it is believed that the commercially preferred pressure range is from about 700 to about 2300 psia.

The examples below also demonstrate that the temperature effects turnover. These examples demonstrate that the catalyst functions, although very poorly, at 23° C. The catalyst functions better at temperatures of 80° C. and higher. The preferred range is from about 160° C. to about 200° C., and the most preferred temperature is about 180° C.

As shown in example 14 below, excellent results are obtained at about 2000 psia and about 180° C. using a dianionic ruthenium catalyst.

EXAMPLES 1-25

In the following examples below, two moles of methanol were reacted with carbon monoxide using the indicated catalyst and reaction conditions. The results are indicated in terms of turnover number which is the number of moles of methyl formate divided by the moles of catalyst divided by the reaction time. The reactions were conducted in a 300 ml. stainless steel autoclave with a glass liner. The catalyst and the methanol were placed in the autoclave. The autoclave was flushed three times with carbon monoxide and then pressurized with carbon monoxide. The reactions were allowed to run for the indicated time periods, and the products were subsequently analyzed using a gas chromatograph.

TABLE I

| Ex. # | Catalyst | Reaction Conditions | Reaction Time | Turnover Rate |
|---|---|---|---|---|
| 1 | $NaOCH_3$ (0.884 mmol) | 1000 PSIG 180° C. | 3 hr. | 6.3 |
| 2 | $NaOCH_3$ (29.82 mmol) | 1000 PSIG 80° C. | 1 hr. | 18.5 |
| 3 | $Na_2Ru(CO)_4$ (0.425 mmol) | 1000 PSIG 180° C. | 3 hr. | 50.6 |
| 4 | $Na_3Co(CO)_3$ (0.638 mmol) | 1000 PSIG 180° C. | 3 hr. | 21.8 |
| 5 | $(Bu_4N)_2Os_3(CO)_{11}$ (0.107 mmol) | 1000 PSIG 180° C. | 3 hr. | 55.3 |
| 6 | $K_2Ru(CO)_4$ (6.05 mmol) | 1000 PSIG 80° C. | .5 hr. 1 hr. 2 hr. 3 hr. | 88.6 111.5 60.6 38.8 |
| 7 | $Na_2Fe(CO)_4$ (5.37 mmol) | 1000 PSIG 80° C. | 1 hr. 2 hr. | 23.6 25.4 |
| 8 | $Na_2Fe(CO)_4$ $1.5(C_4H_8O_2)$ (6.63 mmol) | 150 PSIG 180° C. | 1 hr. | 4.8 |
| 9 | $Na_2Fe(CO)_4$ $1.5(C_4H_8O_2)$ (3.61 mmol) | 1000 PSIG 23° C. | 1 hr. | 0.2 |
| 10 | $Na_2Fe(CO)_4$ $1.5(C_4H_8O_2)$ (3.61 mmol) | 1000 PSIG 40° C. | 1 hr. | 1.6 |
| 11 | $Na_2Cr_2(CO)_{10}$ (1.13 mmol) | 1000 PSIG 180° C. | 1 hr. | 38.62 |
| 12 | $[(Ph_3P)_2N]$ $CoRu_3(CO)_{13}$ (0.38 mmol) | 1000 PSIG 180° C. | 1 hr. | 16.8 |
| 13 | $(PNP)_2Ru_4(CO)_{13}$ (0.018 mmol) | 2100 PSIG (CO/H(1:1)) 160° C. | 22.5 hr. | 35.4 |
| 14 | $(PNP)_2Ru_4(CO)_{13}$ (0.024 mmol) | 2000 PSIG 180° C. | 6.5 hr. | 208.2 |
| 15 | $(PNP)HRu_6(CO)_{18}$ (0.050 mmol) | 2200 PSIG 180° C. | 6 hr. | 85.3 |
| 16 | $(PNP)HRu_6(CO)_{18}$ (0.077 mmol) | 2300 PSIG 180° C. | 9 hr. | 52.4 |
| 17 | $(PNP)_2Ru_6(CO)_{18}$ (0.056 mmol) | 2100 PSIG 180° C. | 7 hr. | 87.0 |
| 18 | $(PNP)_2Ru_6(CO)_{18}$ (0.018 mmol) | 2000 PSIG 160° C. | 21 hr. | 82.9 |
| 19 | $[(Ph_3P)_2N]$ $H_3Ru_4(CO)_{12}$ (0.095 mmol) | 1000 PSIG 180° C. | 3 hr. | 67.7 |
| 20 | $[(Ph_3P)_2N]$ $H_3Ru_4(CO)_{12}$ (0.030 mmol) | 1000 PSIG 180° C. | 3 hr. | 80.8 |
| 21 | $Ru_3(CO)_{12}$ (0.53 mmol) | 1000 PSIG 180° C. | 1 hr. 2 hr. | 7.1 9.7 |
| 22 | $H_2Ru_4(CO)_{13}$ (0.53 mmol) | 2300 PSIG 180° C. | 22 hr. | 11.8 |
| 23 | $H_2Ru_6(CO)_{18}$ (0.016 mmol) | 2400 PSIG 180° C. | 22 hr. | 2.2 |
| 24 | $H_4Ru_4(CO)_{12}$ (0.066 mmol) | 1000 PSIG 180° C. | 3 hr. | 11.2 |
| 25[1] | $(PNP)_2Ru_4(CO)_{13}$ (0.063 mmol) | 2200 PSIG 200° C. | 6 hr. | 3 |

[1] MeOH (3 ml) dissolved in 60 ml/THF.

In the preceding Table, the Examples 1 and 2 are examples of the prior art commercial system using sodium methoxide as a catalyst. Examples 3-20 are examples of the present invention.

Examples 21-24 demonstrate the use of catalysts which are not anionic. As is apparent from these examples, the turnover numbers obtained in Examples 1 and 2 and 21-24 are substantially lower than those obtained using anionic catalysts in Examples 3-20. Example 25 is an example showing the effect of using lower concentrations of methanol in the reaction. In this reaction, a solution containing 3 ml. of methanol and 60 ml. of tetrahydrafuran are used. The turnover number in this example is 3. Accordingly, it indicates that the concentration of methanol should be maintained at higher concentrations, at least about 15 molar percent, and preferably, substantially pure or neat methanol. One additional example of note is Example 13 showing a use of carbon monoxide mixed with hydrogen in a 1:1 ratio being used. Although the turnover number is reduced, it is still better than prior art systems.

EXAMPLE 26

In a 300 ml. stainless steel autoclave with a glass liner, 0.1218 g (0.0556 mmol) of $[(Ph_3P)_2N]_2Ru_6(CO)_{18}$ and 70 ml. of anhydrous methanol were placed. The autoclave was flushed three times with carbon monoxide, pressurized with 1400 psig of carbon monoxide, and heated to 180° C. with stirring. The reaction was allowed to proceed for seven hours. The total pressure changed was from 2100 psig to 1950 psig at 180° C. in this period of time. The reactor was cooled and the gas was vented. Gas chromatographic analysis of the 69.5 ml. methanol solution indicated the 33.84 mmol methyl formate was formed, and the selectivity was 99%.

Of the catalysts shown above, of particular importance are the dianionic ruthenium compounds. The iron compounds are significantly more reactive than expected. These are particularly important since the iron catalysts are currently less expensive than any other catalyst useful in practicing the present invention.

These examples demonstrate that anionic compounds disclosed in formulas I, II and III catalyze the carbonylation of methanol at relatively low pressures, and temperatures with high selectivity and excellent turnover number.

Having thus described our invention, we claim:

1. A method of producing methyl formate from methanol and carbon monoxide at pressures less than about 3,000 psia comprising reacting a an anhydrous solution of methanol comprising at least about 15 molar percent methanol with carbon monoxide in the presence of a catalyst wherein said catalyst has the following general formula:

$$M^{+n} [H_y A'_Q A_x(L)_z]^{-n}$$

wherein
M is a cation;
n is an integer greater than or equal to 1 and less than or equal to 6;
y is an integer greater than or equal to 0 to less than or equal to 4;
A is one or more transition metals selected from the group consisting of Fe, Ru, Os, W, Mo, Cr, Co, Rh, and Ir:
x is an integer greater than or equal to 1;
A' is a Group VIII transition metal;
Q is an integer greater than or equal to 0;
X and Q combined is less than or equal to 36;
L is a ligand; and
z is an integer less than or equal to the available coordination bonding sites of the transition metals represented by $A'_Q A_x$.

2. The method claimed in claim 1 wherein the reaction is conducted at less than about 2300 psia.

3. The method claimed in claim 2 wherein A is Fe or Ru and Q is 0.

4. The method claimed in claim 3 wherein n is an integer greater than or equal to 2.

5. The method claimed in claim 2 wherein said catalyst is selected from the group consisting of:

$$M^{+2} [Ru(CO)_4]^{-2}$$

$$M^{+2} [Ru_4(CO)_{13}]^{-2}$$

$$M^{+2} [Fe(CO)_4]^{-2}.$$

6. A method of forming methyl formate from methanol and carbon monoxide at pressures less than about 2300 psia comprising reacting a an anhydrous solution of methanol which is at least about 15 molar percent methanol with hydrogen and carbon monoxide in the presence of a catalyst selected from the group consisting of:

$$M^{+2} [Ru(CO)_4]^{-2}$$
$$M^{+2} [Ru_4(CO)_{13}]^{-2}$$
$$M^{+2} [Fe(CO)_4]^{-2}$$

wherein M is a cation.

7. A method of producing methyl formate from methanol and carbon monoxide at pressures less than about 3,000 psia comprising reacting a an anhydrous solution of methanol comprising at least about 15 molar percent methanol with carbon monoxide in the presence of a catalyst wherein said catalyst has the following general formula:

$$M^{+n} [H_y A_x (L)_z]^{-n}$$

wherein
M is a cation;
n is an integer greater than or equal to 1 and less than or equal to 6;
y is an integer greater than or equal to 0 and less than or equal to 4;
A is one or more transition metals selected from the group consisting of Fe, Ru, Os, W, Mo, Cr, Co, Rh and Ir;
x is an integer from 1 to 36;
L is a ligand; and
z is an integer less than or equal to the available coordination bonding sites of the transition metals represented by $A_x$.

8. The method claimed in claim 7 wherein A represents Ru and n is greater than 1.

9. The method claimed in claim 8 wherein said catalyst is selected from the group consisting of $$M^{+2} [Ru(CO)_4]^{-2}$$

$$M^{+2} [Ru_4(CO)_{13}]^{-2}$$

$$M^{+2} [Ru_6(CO)_{18}]^{-2}$$

10. The method claimed in claim 9 wherein said catalyst consists of $$M^{+2} [Ru_6(CO)_{18}]^{-2}.$$

11. The method claimed in claim 7 wherein A represents Fe.

12. The method claimed in claim 11 wherein said catalyst consists of $M^{+2} [Fe(CO)_4]^{-2}$.

* * * * *